United States Patent
Mentak

(10) Patent No.: US 7,771,470 B2
(45) Date of Patent: Aug. 10, 2010

(54) OPHTHALMIC APPARATUSES AND METHODS

(75) Inventor: Khalid Mentak, San Ramon, CA (US)

(73) Assignee: Key Medical Technologies, Inc., San Ramon, CA (US)

(*) Notice: Subject to any disclaimer, the term of this patent is extended or adjusted under 35 U.S.C. 154(b) by 1012 days.

(21) Appl. No.: 11/381,891

(22) Filed: May 5, 2006

(65) Prior Publication Data

US 2007/0004852 A1    Jan. 4, 2007

Related U.S. Application Data

(60) Provisional application No. 60/677,917, filed on May 5, 2005.

(51) Int. Cl.
*A61F 2/16* (2006.01)
*G02C 7/02* (2006.01)
*G02B 1/04* (2006.01)
*C09B 62/00* (2006.01)
*C08F 2/00* (2006.01)
*A61L 33/00* (2006.01)
*B05D 5/06* (2006.01)

(52) U.S. Cl. .............. 623/6.11; 623/6.13; 351/159; 351/166; 351/171; 523/106; 526/72; 546/129; 427/2.24; 427/162

(58) Field of Classification Search ........... 524/556; 428/447; 623/6.11, 6.13; 351/159, 171, 351/166; 523/106; 540/129; 526/72; 427/2.24, 427/162

See application file for complete search history.

(56) References Cited

U.S. PATENT DOCUMENTS

| 4,304,895 A | 12/1981 | Loshaek |
| 4,528,311 A | 7/1985 | Beard et al. |
| 4,856,889 A | 8/1989 | Guilino et al. |
| 4,961,746 A | 10/1990 | Lim et al. |
| 5,374,663 A | 12/1994 | Daicho et al. |
| 5,470,932 A | 11/1995 | Jinkerson |
| 5,528,322 A | 6/1996 | Jinkerson |
| 5,543,504 A | 8/1996 | Jinkerson |
| 5,662,707 A | 9/1997 | Jinkerson |
| 5,861,934 A | 1/1999 | Blum et al. |
| 6,089,711 A | 7/2000 | Blankenbecler et al. |
| 6,138,479 A | 10/2000 | Gille et al. |
| 6,353,069 B1 * | 3/2002 | Freeman et al. .......... 526/319 |
| 6,391,049 B1 | 5/2002 | McNally et al. |
| 6,645,246 B1 | 11/2003 | Weinschenk, III et al. |
| 6,695,880 B1 | 2/2004 | Roffman et al. |
| 6,815,074 B2 * | 11/2004 | Aguado et al. .......... 428/447 |

FOREIGN PATENT DOCUMENTS

| DE | 3428895 A1 | 2/1986 |
| EP | 0331457 A2 | 9/1989 |
| WO | 2005066694 A2 | 7/2005 |

OTHER PUBLICATIONS

International Search Report and Written Opinion from corresponding PCT application (PCT/US06/17441), Jan. 17, 2008.
Acrysof® Natural single piece IOL, Product Monograph © 2004 by Alcon Laboratories, Inc.
Supplementary European Search Report for EP 06752318, mailed on Apr. 12, 2010.

* cited by examiner

*Primary Examiner*—Ling-Sui Choi
*Assistant Examiner*—Monique Peets
(74) *Attorney, Agent, or Firm*—Whyte Hirschboeck Dudek S.C.

(57) ABSTRACT

Blue light blocking chromophore (BLBC) ophthalmic devices are disclosed. In an embodiment, BLBC is relatively concentrated in the device center gradually decreasing to the device edge to create a BLBC gradient.

6 Claims, 1 Drawing Sheet

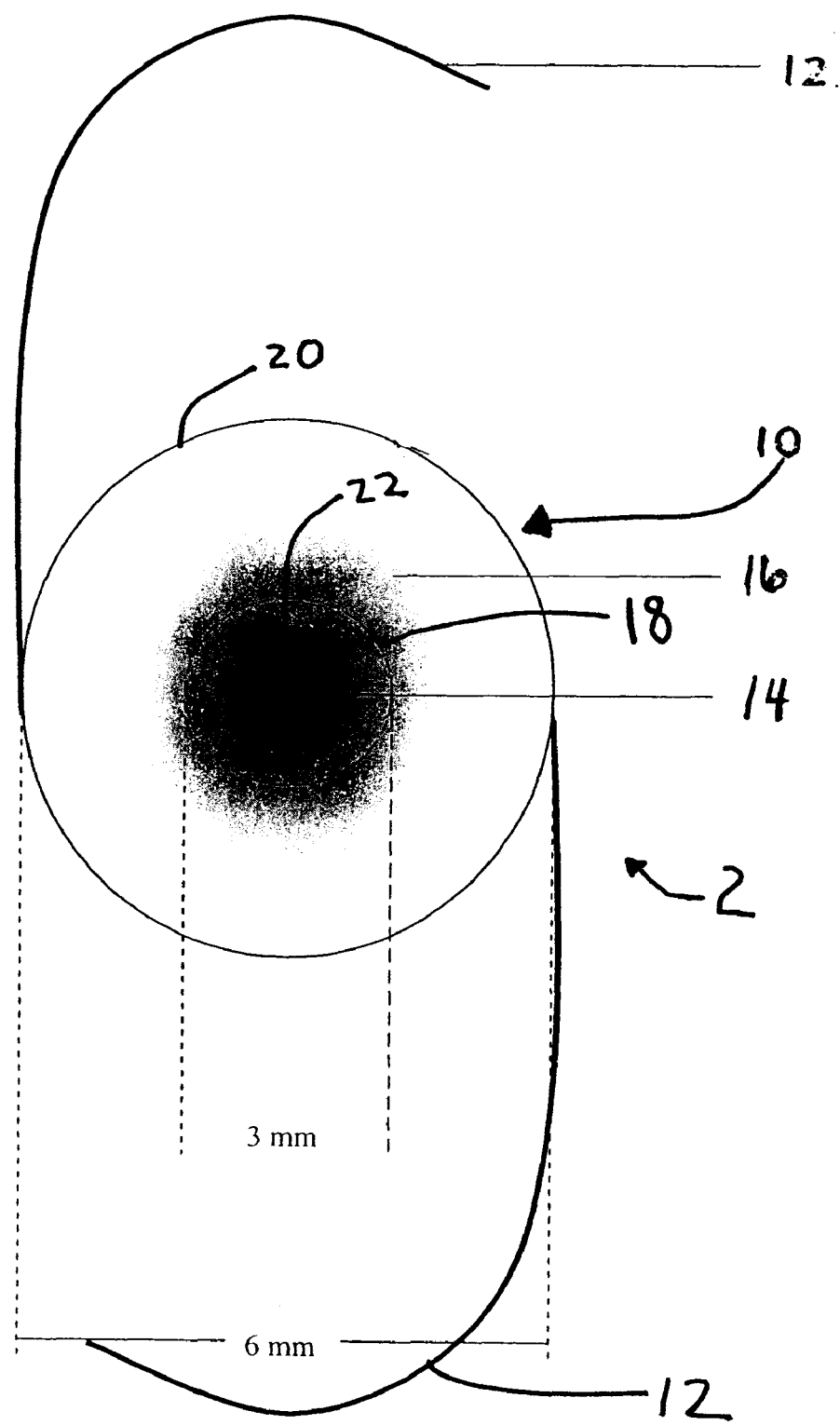
FIGURE

OPHTHALMIC APPARATUSES AND METHODS

INCORPORATION BY REFERENCE AND CROSS REFERENCE TO RELATED APPLICATIONS

Incorporated by reference herein in their entireties are co-pending U.S. Nonprovisional application Ser. No. 11/350,396, filed Feb. 8, 2006 and U.S. Utility application Ser. No. 11/388,212, filed Mar. 23, 2006. This application is related to and claims the benefit of U.S. Provisional Application Ser. No. 60/677,917 filed on May 5, 2005, the contents of which are incorporated herein by reference. Priority is claimed from all three said applications.

FIELD OF INVENTION

This invention relates to ophthalmic devices or apparatuses, particularly intraocular lenses (IOLS), with improved contrast sensitivity and protection from UV and blue light. This invention is particularly applicable to acrylic foldable IOLs and contact lenses. Novel methods of making ophthalmic devices also are disclosed.

BACKGROUND OF THE INVENTION

The assessment of optical hazards in recent years has led to the recognition of the possible hazards to the retina associated with blue light. Generally speaking blue light has a wavelength in the range of about 400-500 nm. If the blue light hazard is a real threat to vision, then the UV/visible transmission characteristics of ophthalmic lenses, and intraocular lenses (IOLs) in particular, should be modified to provide adequate protection from blue light hazards encountered in the environment.

In the ambient environment solar radiation is the primary hazard to vision. The sun freely emits UV, visible and IR radiation much of which is absorbed by the atmosphere. The solar radiation that is transmitted through the atmosphere and reaches the earth's surface consists of UV-B radiation (230-300 nm), near UV or UV-A radiation (300-400 nm), visible light (400-700 nm) and near IR radiation (700-1400 nm). The ocular media of man in its normal, healthy state freely transmits near IR and most of the visible spectrum to the retina. UV-B radiation is, however, absorbed by the cornea and does not reach the retina. UV-A, and the blue portion of the visible spectrum can be absorbed by the crystalline lens of the eye depending upon the person's age.

The human crystalline lens changes its UV and visible transmission characteristics as it ages. In infancy the human lens will freely transmit near UV and visible light above 300 nm, but with further aging the action of UV radiation from the environment causes the production of yellow pigments, fluorogens, within the lens. By approximately the age of 54 the lens will not transmit light below 400 nm and the transmission of light between 400 and 500 nm is greatly diminished. As the lens ages it continuously develops a yellow color, increasing its capacity to filter out near UV and blue light.

Currently, IOLs capable of blocking UV and blue light to varying degrees are effective under certain conditions. However, there are some major drawbacks with such IOLs:

1. Patients with blue light blocking IOLs experience reduced vision quality in dim light conditions. The presence of a blue light blocking chromophore in the lens of the IOL interferes with scotopic vision (low light conditions). This is due to the natural reaction of the eye in scotopic conditions where the pupil dilates to accommodate more light. At the same time, a greater amount of IOL surface area is exposed to the incident light causing an incremental increase of blue light filtration efficiency and an overall reduction in contrast sensitivity.
2. The presence of blue light blocking chromophore in e.g., IOLs, reduces contrast sensitivity in some cases.

Due to their yellow color (which the presence of blue light chromophores imparts to IOLs), blue light blocking chromophores in IOLs and other ophthalmic devices may interfere with color perception.

SUMMARY OF THE INVENTION

The present invention relates, e.g., to the use of blue light blocking chromophores (BLBC) in ophthalmic devices and to a method of lens manufacturing that produce a higher concentration of the e.g., BLBC, at the center of e.g., an IOL, and a relatively lower concentration of the BLBC a the periphery of the IOL. A chromophoric gradient of decreasing chromophore concentration is created from lens center to its edge. The disadvantages associated with existing blue light blocking IOLs are reduced or eliminated by optimizing the interaction of IOL blue light filtering efficiency with pupil size under various light conditions. In intense light conditions (i.e. sunlight, bright artificial light) the pupil is constricted to approximately 3 mm to allow less retinal light exposure. This is known as miosis. The relatively higher chromophore concentration at the center of the lens protects the retina from damage. In dim light conditions, the pupil dilates to approximately 7 mm (or more) to allow more light to reach the retina (mydriasis). The decreasing chromophore concentration from the center of the lens to the edge permits more ambient light to pass through the lens to reach the retina. This, in turn provides enhanced vision quality under dim light conditions.

This invention, in one aspect, permits optimization of the concentration of e.g., BLBC, by creation of a lens-center to lens-edge concentration decline or gradient commensurate with, or selected for, a patient's normal UV, blue light, etc., exposure. One skilled in this art will appreciate that this invention is illustrated by a discussion of IOLs, the invention is not limited to IOLs or any particular chromophore lens or nonchromophoric lens or polymer additive. Put otherwise, the term "additive" is not to be narrowly construed so as to avoid the fundamental nature of this invention. For example, it may be desirable to create a refractive index gradient in accordance with the teaching of the previously incorporated-by-reference Ser. No. 11/388,212 application. The disclosure of the Ser. No. 11/388,212 application relating to creation and definition of an infinite refractive index gradient at page 15 through 17 is specifically incorporated by reference herein. Other such additives where a concentrated gradient, preferably an infinite concentration gradient, will be suggested to one skilled in this and, in view of this invention.

The method of manufacture of the present invention involves the step of creating a central member or core e.g., by polymerization, having a higher concentration of e.g. BLBC, and then polymerizing around the core material a polymer sleeve or tube containing a lesser amount of chromophore, including none. In the second polymerization step at least some of the chromophore tends to migrate from the higher concentration core to the lesser concentration sleeve or perimeter material creating a uniform gradient.

In a variation of the above method an ophthalmic device e.g., an IOL, is created by creating the core material as described above and inserting the core material having a higher concentration chromophore into a lesser-chromophore-containing outer sleeve or rod which has been drilled, machined, laser-modified or otherwise modified, to create a central orifice or hole into which the colored central core is inserted. The structure is completed by bonding the core material to the outer sleeve using such techniques as ultrasonic welding, monomer bonding, or solvent bonding. The structure, thus created, when used to manufacture a lens, has a more abrupt colored-colorless interface or boundary which is useful for some applications.

One skilled in the art will appreciate several things about the above-described method of manufacture. Clearly, the method is not limited to deployment of a chromophore into what will become the lens of e.g. an IOL. Any polymer additive, process enhancer, etc., for which a concentration gradient could provide an advantageous characteristic to the resulting ophthalmic device could be dispersed in a polymer material or property in accordance with this invention. Further, for some applications the concentration gradient or concentration interface could be reversed. Thus, the gradient could have a higher concentration of e.g. a chromophore or other polymer-modifying molecule, additive or comonomer at the edge of e.g. the IOL, with a lesser concentration toward the center of the IOL lens. Generally, of course, care must be taken so that the additive, whatever its purpose, does not leach from the lens structure. For some applications, e.g., administration of a medicament, leach of an additive from a gradient may be intended. All of the above variations are within the contemplation of the present invention.

BRIEF DESCRIPTION OF THE DRAWING

Attached hereto is a FIGURE illustrating an intraocular lens of the present invention which is also produced in accordance with the methods of the present invention.

DETAILED DESCRIPTION OF THE INVENTION

Base Materials

Suitable lens-forming monomers for use in the present invention include carbazole and/or naphthyl moiety, carbazole, naphthalene, or a naphthyl group such as vinyl carbazole, vinyl naphthalene, lauryl methacrylate, stearyl methacrylate, methyl methacrylate, 2-hydroxyethyl acrylate, 2-hydroxyethyl methacrylate, 3-hydroxypropyl acrylate, 3-hydroxypropyl methacrylate, n-vinyl pyrolidone, styrene, eugenol (4-hydroxyvinylbenzene), and .alpha.-methylstyrene. In addition, for high-refractive index foldable lens applications, suitable monomers include, but are not limited to: 2-ethylphenoxy methacrylate, 2-ethylphenoxy acrylate, 2-ethylthiophenyl methacrylate, 2-ethylthiophenylacrylate, 2-ethylaminophenyl methacrylate, phenyl methacrylate, benzyl methacrylate, 2-phenylethyl methacrylate, 3-phenylpropyl methacrylate, 4-phenylbutyl methacrylate, 4-methylphenyl methacrylate, 4-methylbenzyl methacrylate, 2-2-methylphenylethyl methacrylate, 2-3-methylphenylethyl methacrylate, 2-4-methylphenylethyl methacrylate, 2-(4-propylphenyl)ethyl methacrylate, 2-(4-(1-methylethyl)phenyl)ethyl methacrylate, 2-(4-methoxyphenyl)ethyl methacrylate, 2-(4-cyclohexylphenyl)ethyl methacrylate, 2-(2-chlorophenyl) ethyl methacrylate, 2-(3-chlorophenyl)ethyl methacrylate, 2-(4-chloro-phenyl)ethyl methacrylate, 2-(4-bromophenyl)ethyl methacrylate, 2-(3-phenylphenyl)ethyl methacrylate, 2-(4-phenylphenyl)ethyl methacrylate), 2-(4-benzylphenyl)ethyl methacrylate, and the like, including the corresponding methacrylates and acrylates. N-vinyl pyrolidone, styrene, eugenol and .alpha.-methyl styrene may also be suitable for high-refractive index foldable lens applications.

A preferred lens-forming monomer mixture is the mixture of vinyl carbazole, lauryl methacrylate, and hydroxyethyl acrylate.

The copolymerizable cross-linking agent used in the lens-materials of this invention may be any terminally ethylenically unsaturated compound having more than one unsaturated group. Suitable cross-linking agents include, for example: ethylene glycol dimethacrylate, diethylene glycol dimethacrylate, allyl methacrylate, 1,3-propanediol dimethacrylate, allyl methacrylate, 1,6-hexanediol dimethacrylate, 1,4-butanediol dimethacrylate, and the like. A preferred cross-linking agent is ethylene glycol dimethacrylate.

Suitable crosslinkers also include polymeric crosslinkers, such as, polyethylene glycol 1000 diacrylate, polyethylene glycol 1000 dimethacrylate, polyethylene glycol 600 dimethacrylate, polybutanediol 2000 dimethacrylate, polypropylene glycol 1000 diacrylate, polypropylene glycol 1000 dimethacrylate, polytetramethylene glycol 2000 dimethacrylate, and polytetramethylene glycol 2000 diacrylate.

An ultra-violet absorbing material optionally can be included in the polymeric lenses of this invention in order that the lenses may have an ultraviolet absorbance approximately equivalent to that of the natural lens of the eye. The optional ultraviolet absorbing material can be any compound which absorbs ultraviolet light, i.e., light having a wavelength generally shorter than about 400 nm, but does not absorb any substantial amount of visible light. In one approach the ultraviolet absorbing compound generally is added to and dispersed into the monomer mixture prior to polymerization and is entrapped in the polymer matrix when the monomer mixture is polymerized. Suitable ultraviolet absorbing compounds include vinyl anthracene, substituted benzophenones, such as 2-hydroxybenzophenone, and 2-(2-hydroxyphenyl) benzo-triazoles. It is preferred to use an ultraviolet absorbing compound which is copolymerizable with the monomers and is thereby covalently bound to the polymer matrix. In this way possible leaching of the ultraviolet absorbing compound out of the lens and into the interior of the eye is minimized. Suitable copolymerizable ultraviolet absorbing compounds are the substituted 2-hydroxybenzophenones disclosed in U.S. Pat. No. 4,304,895 and the 2-hydroxy-5-acryloxyphenyl-2H-benzotriazoles disclosed in U.S. Pat. No. 4,528,311 both of which are incorporated by reference herein in their entireties. The most preferred ultraviolet absorbing compounds are 2-(3'-methallyl-2'-hydroxy-5'methyl phenyl)benzotriazole and vinyl anthracene.

BLBCs (Blue Light Blocking Chromophores)

BLBC material can be any compound which absorbs violet/blue light, i.e., light having a wavelength between about 380 nm and about 570 mn and which can be adequately bound, e.g., by polymerization, absorption, adsorption, formation of covalent/ionic linkages, etc., to the base polymer. Yellow and orange dyes, polymerizeable yellow and orange dyes, chromene, and any combination thereof are well known BLBC compounds which find uses herein. A list of preferred orange chromophores is set forth at paragraph 8 of the previously incorporated-by-reference Ser. No. 11/350,396 application, that list being specifically incorporated herein. Many such BLBCs will be readily suggested to one skilled in the art in view of this invention. The preferred BLBC is a combination of vinyl anthracene and disperse orange 3 methacrylamide.

Methods of Manufacture

Two methods are described to create the products of the present invention.

Method I:
1. The first step involves the production of the core material at the center of the IOL, which contains a higher concentration of BLBC. A rod measuring approximately 6 inches in length and 3 mm in diameter is produced by polymerizing a base polymer containing 0.005% to 10% of BLBC in a Teflon mold. The polymer rod is removed from the mold cured and annealed for further processing.

The second step involves placing the rod produced in step 1 in a center of a cylindrical mold measuring 6 inches in length and 8 mm in diameter. A solution of the base polymer with no BLBC is polymerized around the 3 mm rod to create a final polymer rod measuring 6 inches in length and 8 mm in diameter and having a maximum concentration of BLBC at the center of the rod.

The polymer rod is machined into 17 mm×2 mm disks and IOLs were cut from the samples. This method creates IOLs with a gradient blue light blocking due to the diffusion of the monomer into the 3 mm rod during the second polymerization.

Method II:
1. The first step of this method is the same as the first step of Method I.
2. The second step involves producing a base polymer rod containing no BLBC measuring approximately 6 inches in length and 8 mm in diameter by polymerizing the base polymer in a Teflon mold. The rod is removed from the mold and a 3 mm hole is drilled in the center of the rod. The 3 mm rod prepared in step 1 is placed inside the hole drilled previously and the two materials bonded together using methods known in the art such as ultrasonic welding, monomer bonding, or solvent bonding.

The polymer rod is machined into 17 mm×2 mm disks and IOLs were cut from the samples. This method creates IOLs with two distinct BLBC concentration zones.

EXAMPLES 1-10

| Monomer | Con | RI | % T at center of lens | | | % T at 3.5 mm from center | | | % T at 5.5 mm from center | | |
|---|---|---|---|---|---|---|---|---|---|---|---|
| | | | 400 nm | 420 nm | 470 nm | 400 nm | 420 nm | 470 nm | 400 nm | 420 nm | 470 nm |
| VC | 30 | 1.569 | 2 | 15 | 58 | 4 | 20 | 68 | 10 | 62 | 75 |
| LM | 37 | | | | | | | | | | |
| HEMA | 30 | | | | | | | | | | |
| EGDM | 2.92 | | | | | | | | | | |
| DYA | 0.08 | | | | | | | | | | |
| VC | 30 | 1.568 | 3 | 14 | 56 | 5 | 21 | 70 | 12 | 65 | 78 |
| LM | 37 | | | | | | | | | | |
| HEA | 30 | | | | | | | | | | |
| EGDM | 2.92 | | | | | | | | | | |
| DYA | 0.08 | | | | | | | | | | |
| VC | 30 | 1.563 | 5 | 20 | 60 | 8 | 30 | 74 | 14 | 68 | 78 |
| EHA | 37 | | | | | | | | | | |
| HEMA | 30 | | | | | | | | | | |
| EGDM | 2.95 | | | | | | | | | | |
| DYM | 0.05 | | | | | | | | | | |
| VC | 30 | 1.562 | 6 | 16 | 61 | 10 | 28 | 73 | 14 | 63 | 77 |
| EHA | 37 | | | | | | | | | | |
| HEA | 30 | | | | | | | | | | |
| EGDM | 2.95 | | | | | | | | | | |
| DYM | 0.05 | | | | | | | | | | |
| VN | 30 | 1.554 | 2 | 4 | 45 | 5 | 10 | 55 | 10 | 58 | 72 |
| EHA | 37 | | | | | | | | | | |
| HEMA | 30 | | | | | | | | | | |
| EGDM | 2.95 | | | | | | | | | | |
| DYM | 0.05 | | | | | | | | | | |
| VC | 29 | 1.551 | 1 | 2 | 48 | 5 | 12 | 60 | 12 | 54 | 70 |
| EHA | 37 | | | | | | | | | | |
| HEA | 30 | | | | | | | | | | |
| EGDM | 2.98 | | | | | | | | | | |
| DOA | 0.02 | | | | | | | | | | |
| VA | 1.0 | | | | | | | | | | |
| PREFFERED FORMULATIONS | | | | | | | | | | | |
| VC | 21.3 | 1.539 | 1 | 19 | 62 | 3 | 39 | 78 | 12 | 64 | 85 |
| HEA | 28.0 | | | | | | | | | | |
| LM | 46.7 | | | | | | | | | | |
| EGDM | 2.985 | | | | | | | | | | |
| DOM | 0.015 | | | | | | | | | | |
| VA | 0.7 | | | | | | | | | | |
| MEB | 0.3 | | | | | | | | | | |
| VC | 21.3 | 1.536 | 1 | 15 | 60 | 3 | 43 | 78 | 15 | 66 | 85 |
| HEA | 28.0 | | | | | | | | | | |
| LM | 46.7 | | | | | | | | | | |

-continued

| Monomer | Con | RI | % T at center of lens | | | % T at 3.5 mm from center | | | % T at 5.5 mm from center | | |
| --- | --- | --- | --- | --- | --- | --- | --- | --- | --- | --- | --- |
| | | | 400 nm | 420 nm | 470 nm | 400 nm | 420 nm | 470 nm | 400 nm | 420 nm | 470 nm |
| EGDM | 2.982 | | | | | | | | | | |
| DOM | 0.018 | | | | | | | | | | |
| VA | 0.7 | | | | | | | | | | |
| MEB | 0.3 | | | | | | | | | | |
| VC | 21.3 | 1.535 | 1 | 14 | 50 | 3 | 32 | 70 | 12 | 67 | 84 |
| HEA | 28.0 | | | | | | | | | | |
| LM | 46.7 | | | | | | | | | | |
| EGDM | 2.97 | | | | | | | | | | |
| DOM | 0.03 | | | | | | | | | | |
| VA | 0.7 | | | | | | | | | | |
| MEB | 0.3 | | | | | | | | | | |
| VC | 21.3 | 1.537 | 1 | 19 | 55 | 3 | 42 | 75 | 12 | 63 | 86 |
| HEA | 28.0 | | | | | | | | | | |
| LM | 46.7 | | | | | | | | | | |
| EGDM | 2.98 | | | | | | | | | | |
| DOM | 0.02 | | | | | | | | | | |
| VA | 0.7 | | | | | | | | | | |
| MEB | 0.3 | | | | | | | | | | |

% T = percent Transmission
VC: vinyl carbazole
VN: 2-vinyl naphthalene
EHA: 2-ethylhexylacrylate
LM: Lauryl methacrylate
HEMA; Hyroxyethylmethacrylate
HEA: Hydroxyethylacrylate
EGDM: ethylene glycol dimethacrylate
VA: vinyl anthracene
MEB: 2-(2'-Methacryloxy-5' methylphenyl)benzotriazole
DYA: Disperse Yellow 7 Acrylate
DYM: Disperse Yellow 7 methacrylate
DOM: Disperse Orange 3 Methacrylamide General Preparation Steps for Polymers of Example 1-10

STEP 1: The comonomers listed above were mixed in a glass flask using a magnetic stir bar for at least 30 minutes followed by sonication, as discussed below, for the times indicated, and then stirring again for another 30 minutes. The combination of sonication and hydrophilic/hydrophobic repulsion forces allows the formation of nanoclusters. The size of the nanoclusters is theoretically controlled by the amount of energy provided during these steps. Sonication for about 30 minutes at a power setting of 100% on a Branson 5510 provides optically clear materials with adequate optical and physical properties. ABIN was added at a concentration of 0.2%. The comonomer mixture with BLBC was vacuum degassed and placed in a Teflon tubular mold. The mold was placed in water bath at 70° C. for 12 hours than cured at 100° C. for 12 hours. A polymer rod measuring 3 mm in diameter and 6 inches in length was removed from the mold, cured and annealed for further processing.

STEP 2: The rod produced in step 1 was placed in a center of a cylindrical mold measuring 6 inches in length and 8 mm in diameter. A solution of the base polymer used in step 1, with no BLBC, and with 0.2% ABIN was poured around the 3 mm rod produced in step 1 and cured similarly to step 1. A final polymer rod measuring 6 inches in length and 8 mm in diameter and having a maximum concentration of BLBC at the center of the rod was produced The polymer rod was machined into 17 mm×2 mm disks and IOLs were cut from the samples.

The refractive index was measured using a CLR 12-70 refractometer from Index Instrument. The optical properties of the IOLs were measured by UV/VIS spectroscopy using a DU-50 spectrophotometer from Beckman Instruments. To asses the efficiency of UV light and blue light blocking at various locations from the center of the lens, which represents eye exposure to different light conditions due to pupil size, light transmittance at key wavelengths was measured at three distances from the center of the IOL: 0 mm (center of the lens), 3.5 mm (just outside light exposure area when the light intensity is at maximum), and at 5.5 mm at the periphery of the lens when the pupil is fully dilated.

The results show that maximum blue light filtration with this novel material occurs at the center of the lens representing a constricted pupil. More visible light would be available to the retina when the pupil is dilated.

References made to the attached FIGURE showing an IOL 2. The IOL 10 of the FIGURE has a lens optic or lens body 10 with attached haptics 12. Lens body 10 has an edge 20 and a center 22. The IOL shown in the FIGURE has an overall diameter of approximately 6 mm. Also as shown is a region of concentrated chromophore 14 approximately 3 mm in diameter. The 3 mm concentrated chromophore then is shown to merge into a gradient zone of chromophore at 16 produced as described above. If a more abrupt chromophoric interface or zone is desired as also as described above, that region or interface would be shown by the dotted circle 18 in the center of the lens optic 10. It is a lens optic 10, a part or portion of an ophthalmic device (i.e., IOL 12) that can be produced in a practice of this invention. As is noted above, while this invention is illustrated using chromophores and intraocular lenses, its teachings and disclosure are by no means intended to be limited thereto.

Incorporation by Reference

Incorporated herein by reference are the following patents and product description:

U.S. Pat. No. 4,304,895 Loshaek
U.S. Pat. No. 4,528,311 Beard
U.S. Pat. No. 5,374,663 Daicho
U.S. Pat. No. 5,470,932 Jinkerson
U.S. Pat. No. 5,528,322 Jinkerson
U.S. Pat. No. 5,543,504 Jinkerson
U.S. Pat. No. 5,662,707 Jinkerson
"Acrysof® Natural single piece IOL , Product Monograph ©2004 by Alcon Laboratories, Inc.

What is claimed is:

1. A method for making a polymeric ophthalmic device intraocular lens (IOL), the IOL having a lens edge and a lens center and a concentration gradient of a polymer additive, the method comprising the steps of:
   providing at least a polymer core, the core having a first concentration of the additive and being adapted to comprise at least part of the ophthalmic device;
   suspending the core in an ophthalmic device a monomer solution comprising monomer and a second concentration of the additive;
   reacting the monomer solution with the polymer core to create the at least part of the ophthalmic device having a concentration gradient of the polymer-modifying additive, wherein the first concentration of additive is higher than the second concentration of additive so that the additive concentration gradient of the lens increases from lens edge to lens center.

2. A method according to claim 1 wherein the additive is a chromophore.

3. A method according to claim 1 wherein the additive is a BLBC.

4. A method for making a polymeric ophthalmic device intraocular lens (IOL), the IOL having a lens edge and a lens center and a concentration gradient of a polymer additive, the method comprising the steps of:
   providing at least a polymer core, the core having a first concentration of the additive and being adapted to comprise at least part of the ophthalmic device;
   suspending the core in an ophthalmic device a monomer solution comprising monomer and a second concentration of the additive;
   reacting the monomer solution with the polymer core to create the at least part of the ophthalmic device having a concentration gradient of the polymer-modifying additive, wherein the first concentration of additive is lower than the second concentration of additive so that the additive concentration gradient decreases from the edge of the lens to the center of the lens.

5. A method according to claim 4 wherein the additive is a chromophore.

6. A method according to claim 4 wherein the additive is a BLBC.

* * * * *